United States Patent
Jang et al.

(10) Patent No.: US 8,161,798 B2
(45) Date of Patent: Apr. 24, 2012

(54) DENSITY SENSING DEVICE AND FUEL CELL SYSTEM WITH IT

(75) Inventors: Won-Hyouk Jang, Yongin-si (KR); Do-Young Kim, Yongin-si (KR); Si-Hyun Lee, Yongin-si (KR); Jung-Kurn Park, Yongin-si (KR); Myeong-Ju Ha, Yongin-si (KR); Sang-Min Jeon, Pohang-si (KR)

(73) Assignees: Samsung SDI Co., Ltd., Gongse-dong, Giheung-gu, Yongin-si, Gyeonggi-do (KR); Postech Foundation, Hyoja-dong, Nam-gu, Pohang-si, Gyeongsangbuk-do (KR)

( * ) Notice: Subject to any disclaimer, the term of this patent is extended or adjusted under 35 U.S.C. 154(b) by 1294 days.

(21) Appl. No.: 11/889,028

(22) Filed: Aug. 8, 2007

(65) Prior Publication Data

US 2008/0044705 A1 Feb. 21, 2008

(30) Foreign Application Priority Data

Aug. 14, 2006 (KR) .................. 10-2006-0076783
Aug. 14, 2006 (KR) .................. 10-2006-0076785
Aug. 14, 2006 (KR) .................. 10-2006-0076786

(51) Int. Cl.
    *G01N 9/00* (2006.01)
(52) U.S. Cl. ............................................. 73/32 R
(58) Field of Classification Search ............... 73/32 R, 73/32 A, 437
    See application file for complete search history.

(56) References Cited

U.S. PATENT DOCUMENTS

| 4,526,480 A | 7/1985 | Ward ........................ 374/117 |
| 6,269,686 B1 | 8/2001 | Hahn et al. ................. 73/54.24 |

(Continued)

FOREIGN PATENT DOCUMENTS

EP 0305133 3/1989

(Continued)

OTHER PUBLICATIONS

The partial European search report issued on Dec. 28, 2007, corresponding to European Patent Application No. 07114351.5-2204.

(Continued)

*Primary Examiner* — Hezron E Williams
*Assistant Examiner* — Tamiko Bellamy
(74) *Attorney, Agent, or Firm* — Robert E. Bushnell, Esq.

(57) ABSTRACT

The disclosed is a density sensing device of a fuel cell system and a fuel cell system having the density sensing device. The density sensing device includes a density sensor that includes a collision sensor and a variable resistor coupled to the collision sensor. The collision sensor is dipped into a fuel solution, and the collisions of molecules of the fuel solution are detected in the collision sensor. The resistance of the variable resistor varies depending on an amount of the collision detected by the collision sensor. The resistance further is converted to a density by the use of a table that includes a relationship between resistance and density. The density sensing device can further include a sensor driver. The sensor driver can be a piezoelectric member that is attached to the collision sensor. The collision sensor vibrates together with the piezoelectric member when a driving signal is applied to the piezoelectric member, which improves the accuracy of the measurement of the density.

15 Claims, 6 Drawing Sheets

U.S. PATENT DOCUMENTS

| | | | |
|---|---|---|---|
| 6,306,285 B1 | 10/2001 | Narayanan | 205/787 |
| 6,389,891 B1 * | 5/2002 | D'Angelico et al. | 73/290 V |
| 6,896,985 B2 | 5/2005 | Horiguchi et al. | 429/444 |
| 2006/0123891 A1 | 6/2006 | Luo et al. | 73/61.61 |

FOREIGN PATENT DOCUMENTS

| | | |
|---|---|---|
| EP | 1 111 703 | 11/2005 |
| GB | 2 401 944 | 11/2004 |
| JP | 2003-294683 | 10/2003 |
| JP | 2005-100864 | 4/2005 |
| JP | 2005-121430 | 5/2005 |
| JP | 2005-207737 | 8/2005 |
| JP | 2005-216687 | 8/2005 |
| KR | 10-2001-0091770 | 10/2001 |
| KR | 10-2002-0056135 | 7/2002 |
| KR | 10-2002-0056137 | 7/2002 |
| KR | 10-0646955 | 11/2006 |
| WO | WO 02/093126 | 11/2002 |

OTHER PUBLICATIONS

*Search report* from the European Patent Office issued in Applicant's corresponding Korean Patent Application No. 07114351.5 dated Feb. 13, 2008.

Korean Notice of Allowance corresponding to Korean Patent Application No. 10-2006-0076783, issued on Jul. 30, 2007.

* cited by examiner

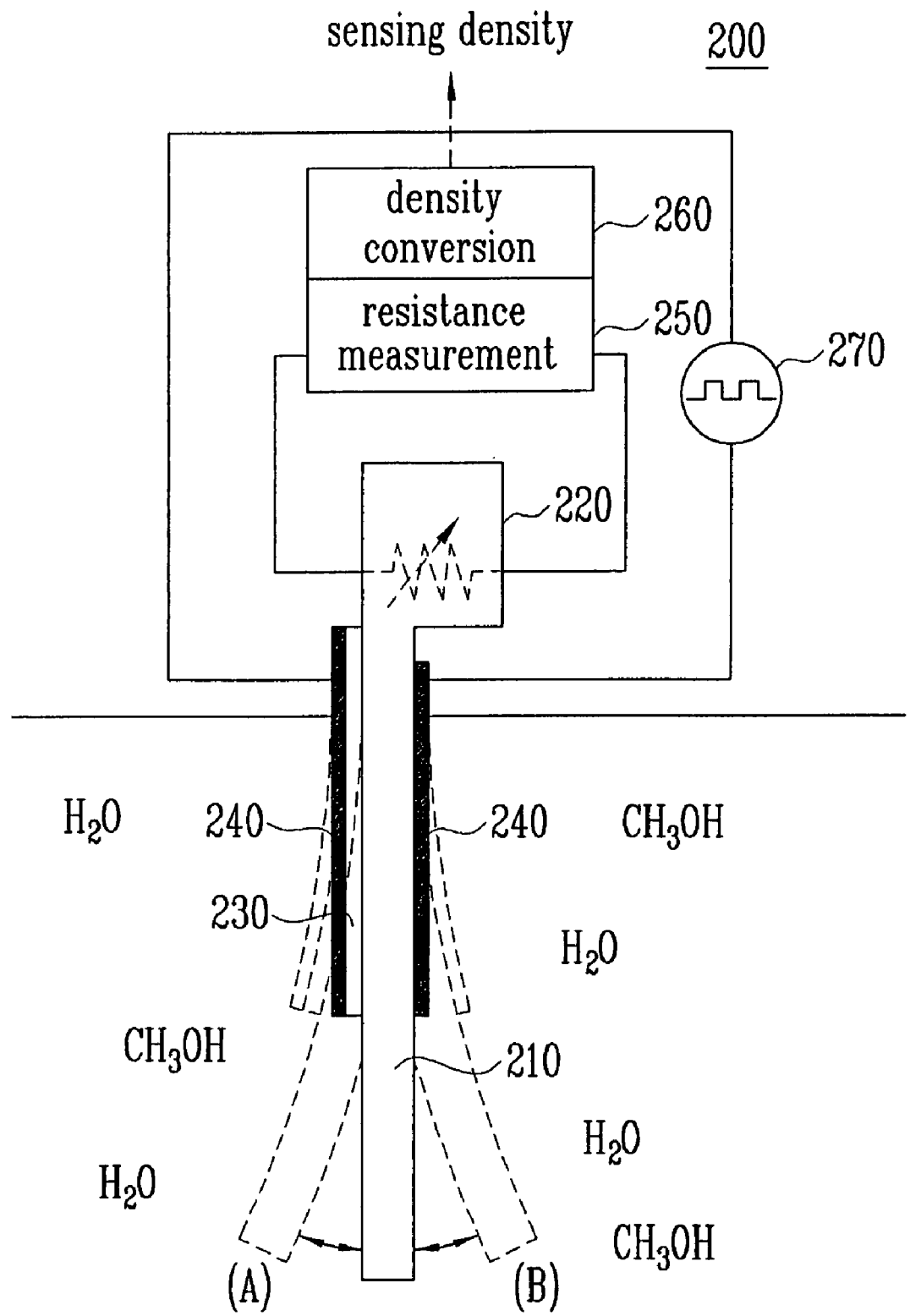

DENSITY SENSING DEVICE AND FUEL CELL SYSTEM WITH IT

CLAIMS OF PRIORITY

This application makes reference to, incorporates the same herein, and claims all benefits accruing under 35 U.S.C. §119 from applications earlier filed in the Korean Intellectual Property Office on the 14$^{th}$ of August 2006 and there duly assigned Serial Nos. 10-2006-0076783, 10-2006-0076785 and 10-2006-0076786.

BACKGROUND OF THE INVENTION

1. Field of the Invention

The present invention relates to a density sensing device, and a fuel cell system having the density sensing device. The present invention, in particular, includes a fuel cell system with a density sensing device that includes a cantilever density sensor.

2. Description of the Related Art

A fuel cell is a power generation system that produces electric energy by electro-chemical reaction between hydrogen and oxygen. Hydrogen is contained in hydrocarbon-based substance such as methanol, ethanol, and natural gas. Oxygen is contained in air.

Depending on types of electrolyte, fuel cells can be categorized into a phosphoric acid fuel cell, a molten carbonate fuel cell, a solid oxide fuel cell, a polymer electrolyte fuel cell, and an alkaline fuel cell, etc. These fuel cells are basically operated by the same principle, but are different in terms of fuel, operation temperature, catalyzer, and electrolyte.

A polymer electrolyte membrane fuel cell (PEMFC) has advantages of a remarkably high output characteristics, low operation temperature characteristics, and rapid starting and responding characteristics over other types of fuel cells. PEMFC is widely used in a mobile power source of portable electronic equipments, in a transportable power source such as a power source for automobile, and in a distributed power source such as a stationary power plant that can be installed in a house or a public building.

A direct methanol fuel cell (DMFC) is similar to the polymer electrolyte membrane fuel cell, but is capable of directly supplying a liquid methanol fuel to a fuel stack. The direct methanol fuel cell is more advantageous in terms of size, because it does not require a reformer, which is required in the polymer electrolyte membrane type fuel cell to obtain hydrogen from fuel.

The direct methanol fuel cell includes a stack, a fuel tank, and a fuel pump. The stack generates electric energy through electrochemical reaction from a fuel, which contains hydrogen and oxidizer such as oxygen.

The stack has a stacked structure of several to several tens unit fuel cells, each of which is typically configured of a membrane electrode assembly (MEA) and a separator. The membrane electrode assembly includes an anode electrode (fuel electrode or oxidation electrode), a cathode electrode (air electrode or reduction electrode), and a polymer electrolyte membrane disposed between the anode electrode and the cathode electrode.

In the fuel cell such as a direct methanol fuel cell in which fuel is supplied to a stack in liquid state, operation efficiency greatly depends on mole density of fuel supplied to an anode electrode and a cathode electrode. For example, if the mole density of the fuel supplied to the anode electrode is high, the amount of the fuel flowing from the anode side to the cathode side increases. Therefore, counter electromotive force is generated due to the fuel reacting on the cathode electrode, so that output voltage decreases. The fuel cell stack has the best operation efficiency at an optimized fuel density. Therefore, a method to properly control a mole density of fuel in the direct methanol fuel cell system has been required for the efficient operation of the fuel cell.

Therefore, the direct methanol fuel cell system or the other type fuel cell systems can include a device for measuring density of a fuel solution stored in units such as a stack, a fuel tank, a recycle tank, or pipes between any two units of the fuel cell system.

In the fuel cell, the operating state of the fuel cell system can be monitored by measuring the density of aqueous fuel solution, and the operation efficiency of the fuel cell can be improved by optimizing condition of each unit forming the fuel cell system according to the monitored result.

Also, in the fuel cell, in which hydrogen is supplied to an anode, such as the polymer electrolyte membrane type fuel cell, there can be a material in a liquid form such as condensate of material released from a cathode side. A density measurement of the liquid material can be provided if necessary.

Therefore, in the fuel cell, the density measurement of solution is important to improve the operation efficiency of the fuel cell. However, in order to install a measurement device for measuring the density of a solution, the density measurement device should satisfy many requirements, such as a small size, an accurate density measurement, a fast density detection, and low cost.

In order to meet the requirements, density sensors, such as a polymer adsorptive density sensor, an ultrasonic type density sensor, and a resistance measurement type density sensor have been proposed. These density sensors, however, do not sufficiently satisfy all the requirements. Therefore, it has been difficult to build a fuel cell system that has high performance and can be manufactured at low cost.

Also, in the case of a small size density sensor, if solid impurities are included in a solution, there is a high possibility that an error would occur in the density measurement due to the presence of the impurities. In particular, in a fuel cell system of a direct methanol fuel cell (DMFC), because there is a very high possibility that the impurities can be included in the fuel while passing through a fuel mixing unit, a device to solve this problem has been required.

Most of the density sensors that have been developed up to now greatly depend on the temperature of the solution to be measured. In order to offset the deviation due to the temperature, two methods have been proposed. One method is to include a separate temperature sensor to measure temperature and a conversion table that shows temperature dependence of the density. Another method is to include a device that keeps the temperature of the solution constant. The first method, however, has problems that the construction of an accurate conversion table is not practical and the adjustment of the conversion table depending on the type of the sensor is not practical. The second method has problems that cost for keeping the temperature of the solution container such as a fuel tank constant is very high.

SUMMARY OF THE INVENTION

The present invention provides solutions for the problems described above. It is an object of the present invention to provide a fuel cell system having a density sensor, which accurately measures density of a fuel solution and is capable of being made at low cost.

It is another object of the present invention to provide a fuel cell system having a density sensor, which measures density of a fuel solution in fast speed.

It is another object of the present invention to provide a density sensing device with a protective chamber and a fuel cell system including the density sensing device, which is capable of preventing a sensing error caused by impurities in a fuel solution.

It is another object of the present invention to provide a density sensing device and a fuel cell system including the density sensing device, which is capable of measuring density of a fuel solution accurately and independently of ambient temperature.

In order to accomplish the objects, there is provided a fuel cell system including a fuel cell stack for generating electric energy through electrochemical reaction of hydrogen and an oxidizer, a fuel supplier for supplying a fuel solution containing hydrogen to the fuel cell stack, an oxidizer supplier for supplying an oxidizer to the fuel cell stack, a density sensor for measuring density of the fuel solution, and a driving controller coupled to the density sensor. The density sensor includes a collision sensor dipped in the fuel solution and a variable resistor coupled to the collision sensor. The collision sensor detects collisions of molecules of the fuel solution. Resistance of the variable resistor varies depending on an amount of the collision detected by the collision sensor. The driving controller controls supply of the fuel solution into the fuel cell stack. The supply of the fuel solution is determined based on data transferred from the density sensor.

The fuel cell system may further includes a sensor driver coupled to the collision sensor. The sensor driver drives the collision sensor to vibrate.

The collision sensor may include a sensing plate. The sensor driver may include a piezoelectric member attached on the sensing plate, and an electrode unit coupled to the piezoelectric member to drive the piezoelectric member.

The fuel cell system may further includes a pulse supplier for supplying a driving pulse to the electrode unit.

The density sensor may include a density computing unit coupled to the variable resistor. The density computing unit computes value of density from the value of the resistance of the variable resistor. The density computing unit may include a resistance measurement unit for measuring the resistance of the variable resistor, and a density converter coupled to the resistance measurement unit. The density converter converts the resistance of the variable resistor into the value of density. The density converter may include a conversion table that includes a relationship between resistance and density. The density converter converts the resistance of the variable resistor into the value of density by looking up the relationship of the conversion table. The density computing unit may further include a temperature measurement unit for measuring temperature at a position at which the density sensor is located.

According to another aspect of the present invention, there is provided a density sensing device of a fuel cell system, which includes a density sensor for measuring a density of a fuel solution of the fuel cell system, and a protective chamber enclosing the density sensor. The protective chamber protects the density sensor from collision with an impurity particle. The protective chamber can be formed in a mesh shape. The protective chamber can be made of a material such as carbon fiber-based material, metal material having a low reactivity with methanol and water, plastic material, or combinations thereof.

According to another aspect of the present invention, there is provided a density sensing device of a fuel cell system, which includes a base frame, a temperature sensor formed on the base frame, a density sensor formed on the base frame, a heating member formed on the base frame, and an isothermal controller coupled to the heating member. The temperature sensor measures temperature of a fuel solution of the fuel cell system. The density sensor measures density of the fuel solution. The heating member partly or completely surrounds both of the temperature sensor and the density sensor. An area enclosing the heating member is formed into a sensing region, and the heating member heats the fuel solution in the sensing region. The isothermal controller controls the heating member in order to keep the temperature of the heating member constant. The base frame may further include a guide unit for keeping the temperature of the fuel solution in the sensing region constant.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein:

FIG. 3B is a diagram showing another active cantilever density sensor constructed as another embodiment of the present invention;

DETAILED DESCRIPTION OF THE INVENTION

Hereinafter, a preferred embodiment of the present invention, wherein a person having ordinary skill in the art can easily carry out the present invention, will be described in a more detailed manner with reference to the accompanying drawings. However, the present invention can be changed in many different equivalent forms, and should not be construed as limited to the embodiments set forth herein.

Hereafter, resistance measurement includes meanings that the outputted result of the resistance measurement is regarded as value of resistance regardless of unit of the outputted result. For example, resistance of a resistor can be represented in a unit of ohm, or can be represented in a unit of voltage when a predetermined magnitude of current flows through the resistor. The resistance of the resistor also can be represented in a unit of current when a predetermined voltage is applied to the resistor. In other words, although a unit of measurement of resistance is different, the result of the resistance measurement is intended to indicate resistance of a resistor presented in the present invention.

Figure 1:
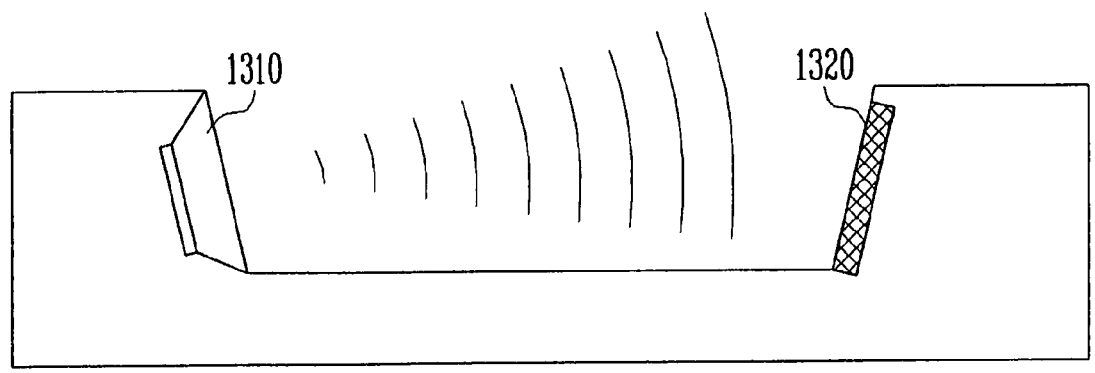
FIG. 1 is a diagram showing a structure of an ultrasonic type density sensor.

FIG. 1 shows a structure of an ultrasonic type density sensor. Ultrasonic waves are generated from ultrasonic generator 1310 into a solution, density of which is to be measured. Detector 1320 located at an opposite side of ultrasonic generator 310 detects the ultrasonic wave interfering with the solution, and density of the solution is obtained.

Figure 2:
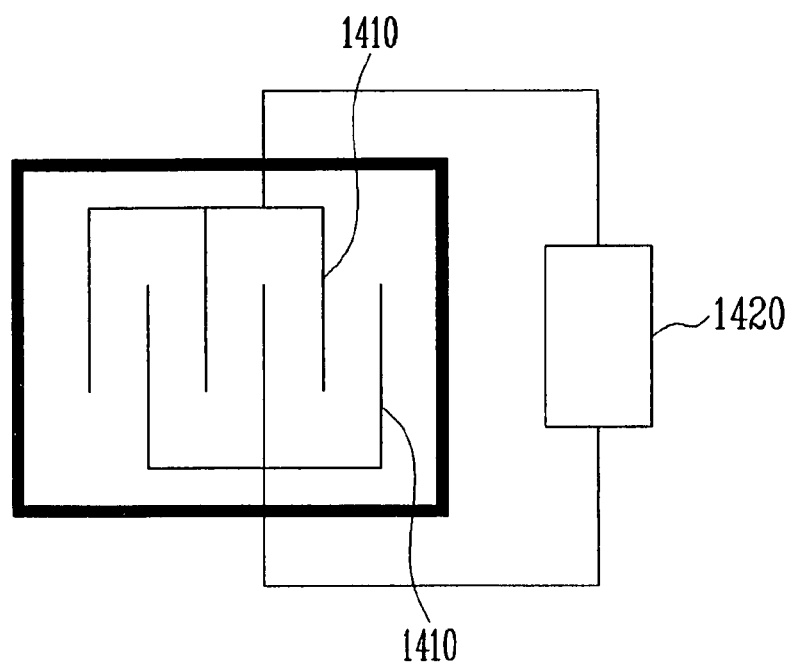
FIG. 2 is a diagram showing a structure of a resistance measurement type density sensor.

FIG. 2 shows a structure of a resistance measurement type density sensor. Density sensor 1420 measures resistance of a solution between electrodes 1410. The density of the solution is obtained from the measured resistance of the solution.

Figure 3A:
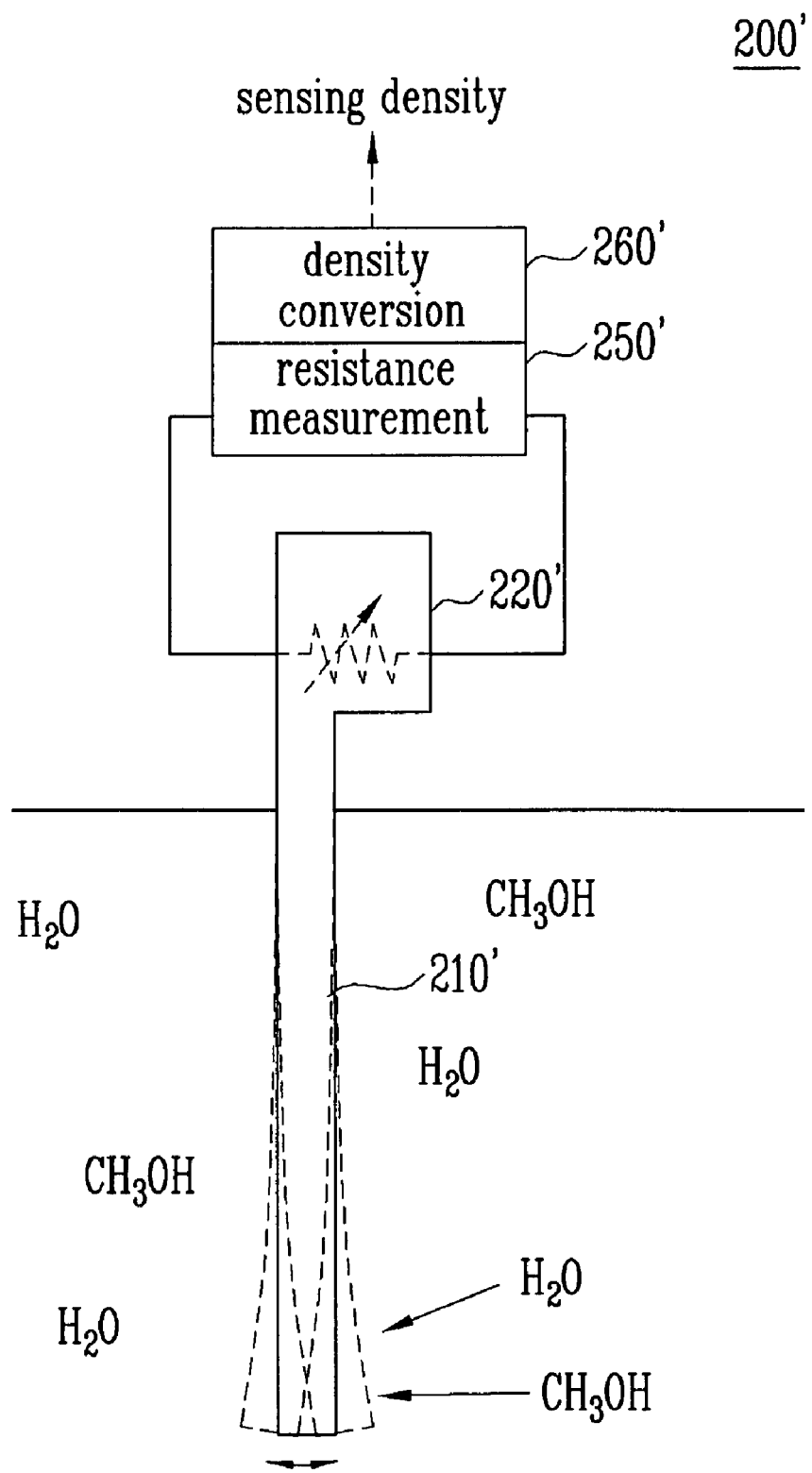
FIG. 3A is a diagram showing an active cantilever density sensor constructed as an embodiment of the present invention.

FIG. 3A shows an active cantilever density sensor constructed as a first embodiment of the present invention. Active cantilever density sensor 200' includes a collision sensor that includes sensing plate 210', variable resistor 220', and a density computing unit that includes resistance measurement unit 250' and density converter 260'. Sensing plate 210' is dipped in a solution, density of which is to be measure, and an end of sensing plate 210' is integrally coupled to variable resistor 220'. Therefore, the integrated structure of sensing plate 210' and variable resistor 220' forms a cantilever structure. Resistance of variable resistor 220' varies depending on the degree of bend of sensing plate 210'. The density computing unit reads the resistance of variable resistor 220', and produces density of the solution.

The principle of cantilever density sensor 200' will be described in detail. A methanol aqueous solution includes water molecules and methanol molecules that are irregularly and constantly moving in the solution. If sensing plate 210' with a sufficiently thin thickness is dipped in a methanol aqueous solution, the water and methanol molecules collide with sensing plate 210'. Therefore, sensing plate 210' is deformed or bent due to the collision, and resistance of variable resistor 220', which is connected to one end of sensing plate 210', changes due to the deformation of sensing plate 210'.

Because the water and methanol molecules are different in terms of molecular weight, the strength of collision applied to sensing plate 210' varies depending on the density of the methanol aqueous solution, generating differences in the degree of the change of the resistance of variable resistor 220'. Therefore, the measurement of the density can be achieved by detecting the degree of the change of the resistance, and by converting the resistance into corresponding value of density. In the first embodiment, sensing plate 210' is employed as a collision sensor. Another type of device, which is capable of providing a change of resistance of a variable resistor, also can be employed as a collision sensor of the present invention.

The density computing unit coupled to variable resistor 220' includes resistance measurement unit 250' and density converter 260'. Resistance measurement unit 250' measures the resistance of variable resistor 220'. Density converter 260' produces value of density from the measured resistance by looking up a conversion relationship between density and resistance.

The entire density computing unit or density converter 260' alone can be implemented in a hardware module, or in a software module, which forms parts of a driving controller that controls the entire operation of a fuel cell system.

Resistance measurement unit 250' outputs an electrical signal, such as voltage and current, in proportion to the resistance value of variable resistance value 220'. Density converter 260' reads the measured resistance value transferred from resistance measurement unit 250', and produces variation of the fluctuation of the resistance value. Value of density is obtained from the variation of the fluctuation of the resistance.

The conversion from the variation of the fluctuation to density can be implemented in an analog circuit that has a simply conversion function. Practically, more accurate density value, however, can be obtained by considering other factors such as temperature of the solution.

In a simplified configuration excluding the temperature effect, position dependent density value can be stored in another conversion table. The position means the position of the collision sensor in a solution. A simplified configuration can be further achieved on the assumption that the density of solution is independent of temperature and independent of position of the collision sensor. In general, density converter 260' can have various resistance to density conversion tables that reflect the dependence of density on temperature and position. Density converter 260' retrieves the density value, which corresponds to the variation of the fluctuation of the resistance, from the conversion table.

If the temperature effect is completely considered, temperature measured by a temperature measurement device, which is installed around the density sensor, can be inputted into density converter 260'. In this case, the density computing unit further includes a temperature measurement unit for measuring temperature of a solution on the position of the density sensor. Then, density converter 260' produces density value that depends on the measured resistance and temperature. Density converter 260' may include a temperature/resistance to density conversion table, and retrieves the density value, which corresponds to the variation of the fluctuation of the resistance, from the conversion table.

The operation of a fuel cell system with the density sensor of the present embodiment is the same as the operation of a fuel cell system with the density sensor of a second embodiment, and will be described in detail while describing the second embodiment.

FIG. 3B shows another active cantilever density sensor constructed as a second embodiment of the present invention. Active cantilever density sensor 200 as show in FIG. 3B includes a collision sensor that includes sensing plate 210, variable resistor 220, and a density computing unit that includes resistance measurement unit 250 and density converter 260. Sensing plate 210 is dipped in a solution, density of which is to be measured, and an end of sensing plate 210 is integrally coupled to variable resistor 220. Therefore, the integrated structure of sensing plate 210 and variable resistor 220 forms a cantilever structure. Resistance of variable resistor 220 varies depending on the degree of bend of sensing plate 210. The density computing unit reads the resistance of variable resistor 220 and produces density of the solution. Active cantilever density sensor 200 of the second embodiment further includes a sensor driver that includes piezoelectric member 230 and electrode unit 240.

In the present embodiment, a collision sensor that detects strength of collision of molecules in a solution is implemented as sensing plate 210 that has a plate shape. If the strength of collision from water molecules and the methanol molecules is too weak, accuracy of the density sensing may reduce. In order to solve this problem, a sensor driver is provided in the present embodiment in order to allow regular vibration of sensing plate 210.

Although the sensor driver can be implemented with a mechanical device such as an electromagnet, it is preferable that the sensor driver is implemented with a piezoelectric element. The piezoelectric element is easy to be manufactured in a tiny size, which will satisfy the requirement of the density sensing device for a fuel cell system. In this case, the sensor driver includes a piezoelectric member 230 bonded to sensing plate 210, and electrode unit 240 to produce electric field that drives piezoelectric member 230.

Piezoelectric member 230 can be bonded on the outside of sensing plate 210, or can be formed inside sensing plate 210. Electrode unit 240 can be configured of two electrode membranes. If sensing plate 210 is made of a conductive material that is capable of holding a reference potential (e.g., ground potential), electrode unit 240 can be configured of one electrode membrane, which is formed on the surface of the piezoelectric member that is opposite to the surface contacting sensing plate. If electrode unit 240 is configured of two electrode membranes, one electrode membrane can be configured to contact sensing plate 210, and the other electrode membrane can be configured to contact piezoelectric member 230, as shown in FIG. 3B. It is also possible that one electrode membrane is formed between sensing plate 210 and piezoelectric member 230, and another electrode membrane is configured to contact piezoelectric member 230.

If a predetermined voltage is applied to electrode unit 240, the length of piezoelectric member 210 changes. Because piezoelectric member 210 is bonded to sensing plate 210, length of which does not change, the stack of piezoelectric member 230 and sensing plate 210 bends in one direction. If compression voltage for piezoelectric member 230 is applied to piezoelectric member 230, piezoelectric member 230 expands, while if expansion voltage for piezoelectric member 230 is applied to piezoelectric member 230, piezoelectric member 230 shrinks. Therefore, if compression voltage is applied to electrode unit 240, sensing plate 210 bends toward position (A) as shown in FIG. 3B. If expansion voltage is applied to electrode unit 240, sensing plate 210 bends toward position (B) as shown in FIG. 3B.

Pulse supplier 270 supplies a driving pulse to electrode unit 240. The magnitude of voltage periodically changes in the driving pulse in order to alternately produce compression voltage and expansion voltage for piezoelectric member 230. Therefore, one end of sensing plate 210 vibrates moving between position (A) and (B). Consequently, the displacement of the vibration according to the driving pulse varies depending on the density of the methanol solution in which sensing plate 210 is dipped. The variation of the displacement of the vibration also has an effect on the variation of the fluctuation of the resistance of variable resistor 220.

The density computing unit connected to variable resistor 220 can be configured of including resistance measurement unit 250 for measuring the resistance of variable resistor 220, and density converter 260 for producing density from the resistance value by the use of density conversion relationship given according to the position of the density sensor. Herein, the entire density computing unit or density converter 260 can be implemented in a hardware module or in a software module, which forms parts of a driving controller controlling the entire operation of a fuel cell system.

Resistance measurement unit 250 outputs an electrical signal such as voltage and current in proportion to the resistance value of variable resistor 220. Density converter 20 receives the output of resistance measurement unit 250, and produces variation of the fluctuation of the resistance, and converts the variation of the fluctuation of the resistance into density.

The conversion from the variation of the fluctuation of the resistance to density can be implemented in an analog circuit that has a simply conversion function. Practically, more accurate density value, however, can be obtained by considering other factors such as temperature of the solution.

In a simplified configuration excluding the temperature effect, position dependent density value can be stored in another conversion table. The position means the position of the collision sensor in a solution. A simplified configuration can be further achieved on the assumption that the density of solution is independent of temperature and independent of position of the collision sensor. In general, density converter 260 can have various resistance to density conversion tables that reflect the dependence of density on temperature and position. Density converter 260 retrieves the density value, which corresponds to the variation of the fluctuation of the resistance, from the conversion table.

If the temperature effect is completely considered, temperature measured by a temperature measurement device, which is installed around the density sensor, can be inputted into density converter 260. In this case, the density computing unit further includes a temperature measurement unit for measuring temperature of a solution on the position of the density sensor. Then, density converter 260 produces density value that depends on the measured resistance and temperature. Density converter 260 may include a temperature/resistance to density conversion table, and retrieves the density value, which corresponds to the variation of the fluctuation of the resistance, from the conversion table.

In the following description, available units in which a collision sensor can be installed and an application process of the density obtained from the density sensing device in a fuel cell system will be described. Herein, the term "non-reacted fuel" means fuel that is exhausted but is not reformed into hydrogen gas, which is performed together with water ($H_2O$) generated while reforming hydrogen-containing fuel into hydrogen gas in a stack of a fuel cell system. The term "raw material" means a high density fuel such as hydrocarbon-based fuel group including methanol, ethanol, and natural gas. The term "hydrogen-containing fuel" means fuel supplied to a reformer or a stack.

Figure 4:
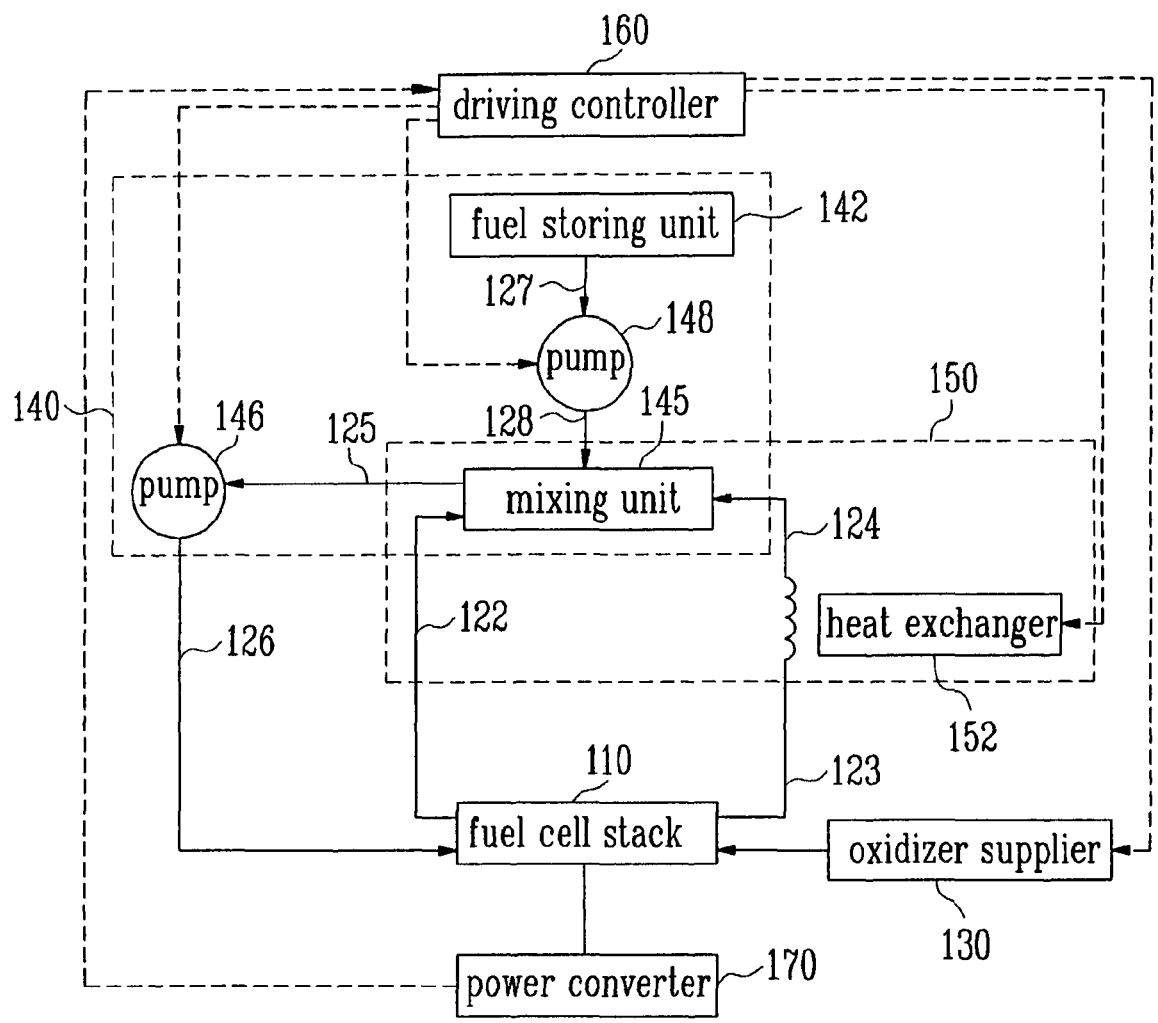
FIG. 4 is a block diagram showing a structure of a direct methanol fuel cell equipped with an active cantilever density sensor of the present invention.

FIG. 4 shows a structure of a direct methanol fuel cell equipped with an active cantilever density sensor of the present invention. The structure shown in FIG. 4, however, is not limited to the fuel cell system that uses methanol for fuel, but the structure is also applicable to a fuel cell system in which fuel in an aqueous solution state is supplied to a stack, such as a fuel cell using ethanol and acetic acid as fuel.

Referring to FIG. 4, a direct methanol type fuel cell includes fuel cell stack 110 for generating electricity by electrochemical reaction between hydrogen gas and oxygen gas, fuel storing unit 142 for storing a high density fuel to be supplied to fuel cell stack 110, oxidizer supplier 130 for supplying oxidizer to fuel cell stack 110, heat exchanger 152 for recovering non-reacted fuel exhausted from stack 10, and mixing unit 145 for supplying fuel to fuel cell stack 110. The fuel supplied to fuel cell stack 110 contains hydrogen produced by mixing the non-reacted fuel exhausted from heat exchanger 152 with the high density fuel exhausted from fuel storing unit 120. Herein, heat exchanger 152 and mixing unit 145 forms effluent processor 150 for processing the effluent of the stack. Fuel storing unit 120, mixing unit 145, and first pump 146 form fuel supplier 140.

Fuel cell stack 110 is provided with a plurality of unit cells that includes a membrane electrode assembly (MEA), which is configured of a cathode electrode, an anode electrode, and a polymer membrane disposed between the cathode electrode and the anode electrode. The anode electrode oxidizes hydrogen gas generated by reforming the hydrogen-containing fuel supplied from fuel supplier 140, generating hydrogen ions ($H^+$) and electrons ($e^-$). The cathode electrode converts oxygen in air supplied from oxidizer supplier 130 into oxygen ions and electrons. Hydrogen ions generated from the anode electrode are provided to the cathode electrode through the polymer membrane. The polymer electrolyte membrane exchanges ions, and prevents transfer of hydrogen-containing fuel. The polymer electrolyte membrane has a thickness of about 50 to 200 μm.

The electricity, which is generated from chemical reaction between hydrogen gas and oxygen in the unit cell, is converted to have standard voltage and current by power converter 170. The electricity with the standard voltage and current is outputted for application. The output of power converter 170 can be used to charge a secondary cell that is separately equipped, or to supply power to driving controller 160.

Non-reacted fuel, in which carbon dioxide ($CO_2$) and water ($H_2O$) are mixed, moves to a condensing unit of heat exchanger 152 through an outlet, and the non-reacted fuel condensed in the condensing unit is collected in mixing unit 145. The carbon dioxide contained in the non-reacted fuel can be exhausted from mixing unit 145 to the outside. After mixing the non-reacted fuel collected in mixing unit 50 with the high density fuel supplied from fuel storing unit 120, the mixture of the non-reacted fuel and the high density fuel is supplied to the anode electrode of fuel cell stack 110.

Oxidizer supplier 30 can be an air supplying means for supplying air as an oxidizer. Oxidizer supplier 30 can be implemented with an active driving pump for supplying air to the cathode electrode of fuel cell stack 110, or can be implemented with a passive vent hole that is a structure designed to make smooth air flow.

Driving controller 160 is provided to control the operation of driving pump 148 (or second pump 148) that is connected to fuel storing unit 142, and the operation of first pump 146 that supplies mixed fuel to fuel cell stack 110. In addition to first and second pumps 146 and 148 described above, additional pumps can be installed in first pipe 123 that connects the cathode of fuel cell stack 110 to heat exchanger 152, second pipe 124 that connects heat exchanger 152 to mixing unit 145, third pipe 122 that connects the anode of fuel cell stack 110 to mixing unit 145, or the inside of oxidizer supplier 130. Driving controller 160 can control the operation of each of the pumps.

It is preferable that driving controller 160 includes a digital processor. The digital processor can have a structure that a reference clock for an operation is inputted. The operation amount of driving controller 160 and the operation amounts of the density computing unit of the present invention are small, and thus, one processor can be implemented to perform both processes of the driving control and the density computation. In order to save a hardware, the pulse supplier for supplying a driving pulse to the electrode unit can be implemented to generate the driving pulse by receiving the reference clock. Also, driving controller 160 can also be implemented to perform the function of resistance measurement unit 250 as shown in FIG. 3B.

The input data, which are required for driving controller 160 to control the operation of pumps, can include density values of each of the unit fuel cell, a state of power (current, voltage, etc.) generated in the power converter, and temperature values of each of the unit fuel cells. Accordingly, the density sensing device of the present invention can be installed in the inside of the system such as mixing unit 145, first and second pumps 146 and 148. The density sensing device also can be installed in a liquid flow path, such as first pipe 123, second pipe 124, third pipe 122, fourth pipe 127 that connects fuel storing unit 142 to second pump 148, fifth pipe 128 that connects second pump 148 to mixing unit 145, input pipe 125 that connects mixing unit 145 to first pump 146, or output pipe 126 that connects first pump 146 to fuel cell stack 110.

Hereafter, the operation of driving controller 160 will be described. As described above, the density sensor can be installed inside various units such as mixing unit or pipes. In the description of the operation of driving controller 160, the density sensor shown in FIG. 3A or 3B is provided inside mixing unit 145 as an example.

If output power from power converter 170 is below a reference power level, driving controller 160 determines that there is a significant load, and increases supply of fuel to fuel cell stack 110 by operating first pump 146 in order to increase the output power. If density of a fuel in mixing unit 145 becomes lower than a predetermined reference level, the amount of condensation of the non-reacted fuel is increased by increasing the operation rate of heat exchanger 152, or the supply of fuel from fuel storing unit 142 is increased by operating second pump 148. On the contrary, if the density of a fuel in the mixing unit 145 becomes higher than the predetermined reference level, the amount of condensation of the non-reacted fuel is decreased by decreasing the operation rate of heat exchanger 152, or the supply of fuel from fuel storing unit 142 is decreased by reducing the operation of second pump 148. Accordingly, the density of hydrogen-containing fuel supplied from mixing unit 145 to the anode electrode of fuel cell stack 110 is kept in constant, enabling stable power generation and high efficiency of the power generation of the fuel cell system.

Figure 5:
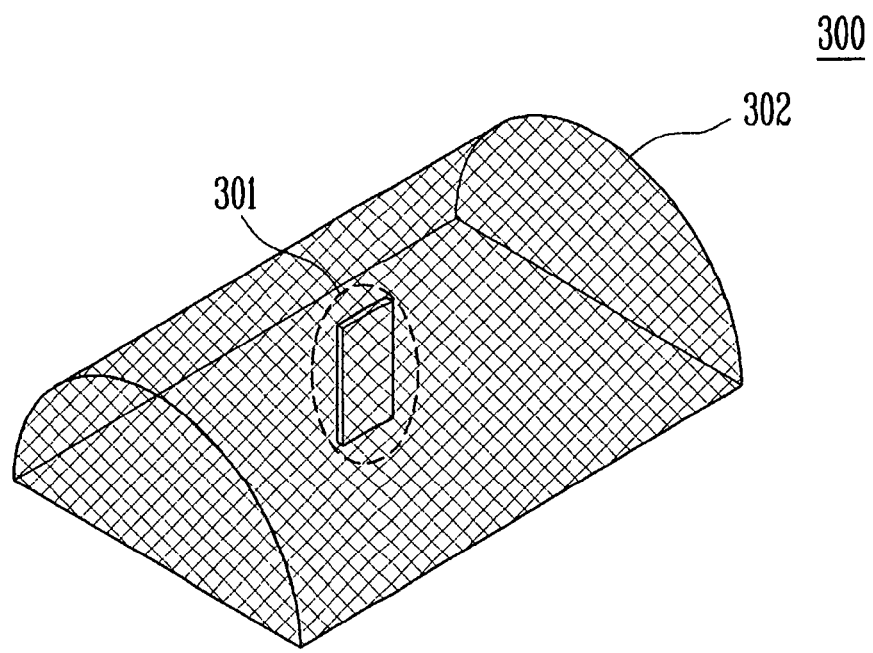
FIG. 5 is a perspective view showing a density sensing device with a protective chamber, which is constructed as another embodiment of the present invention.

FIG. 5 shows a density sensing device having a protective chamber, which is constructed as third embodiment of the present invention. Referring to FIG. 5, density sensing device 300 of the present embodiment includes density sensor 301 and protective chamber 302. Density sensor 301 includes a collision sensor positioned inside a solution to detect the collision of molecules of the solution, and a variable resistor, resistance of which varies depending on the amount of collision detected in the collision sensor. Protective chamber 302 prevents impurity particles from contacting density sensor 301.

Protective chamber 302 is to prevent an error in the density measurement, which can be caused by collisions with impurity particles that are bigger than a predetermined size. It is preferable that protective chamber 302 has a mesh shape. The spaces formed in the surface of the mesh may have a predetermined size to prevent impurity particles bigger than the predetermined size. In this case, it is preferable that, for the purpose of the accuracy of the density measurement, the space size of the mesh can be as small as the size of the particles contained in the solution, density of which is measured. However, if the space size of the mesh is too small, it prevents the solution from flowing in and flowing out of the chamber, and the rate of detecting the change in the density of the solution becomes low. Therefore, the mesh should have a proper space size.

Protective chamber 302 is made of proper materials so that the chamber is not eroded or dissolved in the solution to be measured. For example, in order to use the protective chamber with a sensor for measuring density in methanol that is used in a fuel cell system, the protective chamber can be made of a carbon fiber-based material such as graphite, metal material having a small reactivity of methanol with water such as stainless steel, plastic material such as PET, or combinations thereof.

Density sensor 301 can be any type of density sensors, but it is preferable that the density sensing device is implemented with a cantilever type density sensor described in the first embodiment or the second embodiment.

Therefore, a cantilever density sensor of the first embodiment includes a sensing plate dipped in a solution to be measured, and a density computing unit for producing density that depends on the magnitude of the resistance measured from the variable resistor. The sensing plate is integrally coupled to a variable resistor that is mounted in the density sensing device, and one end of the sensing plate is dipped in the solution. Therefore the structure of the sensing plate forms a cantilever structure.

A cantilever density sensor of the second embodiment includes a sensing plate dipped in a solution to be measured. The sensing plate is integrally coupled to a variable resistor that is mounted in the density sensing device, and one end of the sensing plate is dipped in the solution. Therefore the structure of the sensing plate forms a cantilever structure. The cantilever density sensor of the second embodiment also includes a density computing unit for producing density that depends on the magnitude of the resistance measured from the variable resistor, and a sensor driver for vibrating the sensing plate.

The density sensing device with the protective chamber of the present embodiments can be used for measuring the density of the mixing fuel by being mounted within mixing unit 145 as shown in FIG. 4 or pipes. The details of the application to the fuel cell system are almost the same as the application of the second embodiment, and thus the detailed description thereof will be omitted.

If impurity particles contact the cantilever density sensor, the accuracy of the measurement and the lifetime of the sensor deteriorate. The present embodiment prevents the impurity particles from colliding with the cantilever density sensor by providing the protective chamber. Therefore, the accuracy of the measurement can be improved, and lifetime of the sensor increases.

Figure 6:
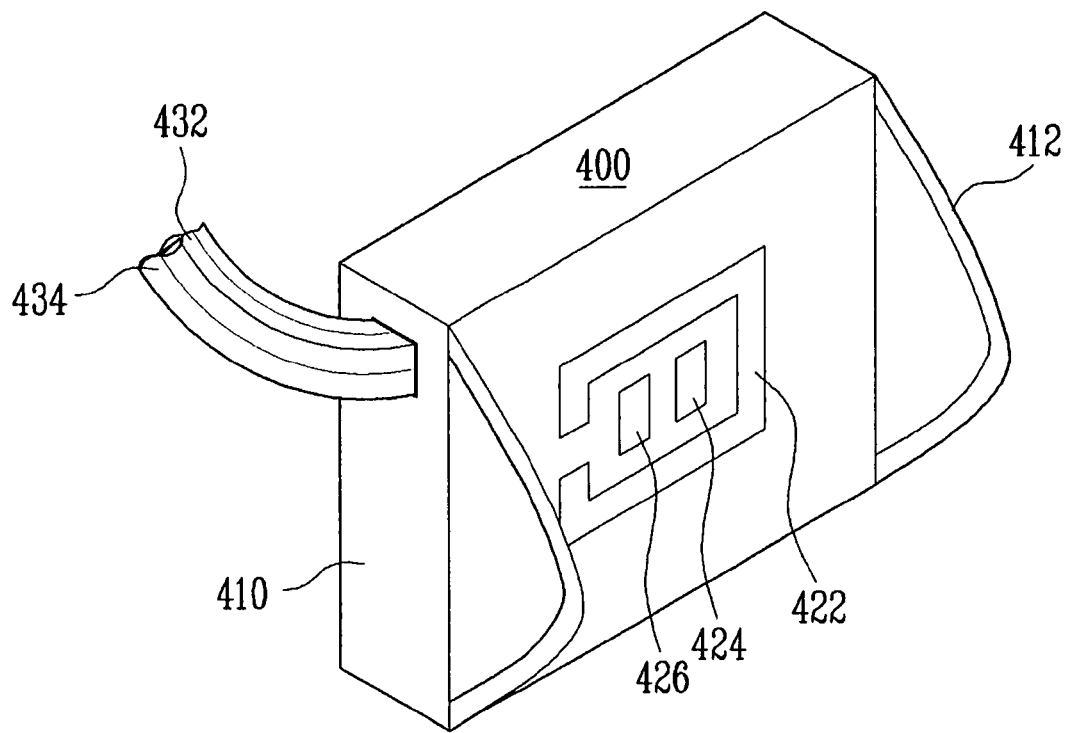
FIG. 6 is a perspective view showing an isothermal density sensing device constructed as another embodiment of the present invention.

FIG. 6 shows an isothermal density sensing device constructed as a fourth embodiment of the present invention. Referring to FIG. 6, density sensing device 400 of the present embodiment has a shape to be mounted on a tank, such as a fuel tank of a fuel cell system or a mixing tank for recovering non-reacted fuel, in which a fuel solution is stored.

One surface of base frame 410 is formed as a plane in order to be easily attached to a bottom or a wall of a tank, and can include a separate attachment means (e.g., a bolt connector) on the plane. The other surface of base frame 410 directly contacts the solution stored in the tank. Density sensor 426, temperature sensor 424, and heating member 424 are installed on the other surface. It is preferable that base frame 410 further includes guide unit 412 to keep the temperature of the solution within a sensing region constant, and therefore to reduce power consumption by heating member 422 and to perform more accurate isothermal control.

Density sensor 426 and temperature sensor 424 are installed in the region heated by heating member 422. In order to minimize the measurement error in the sensing region, it is preferable that heating member 422 is formed to partly or completely surround both of density sensor 426 and temperature sensor 424 as shown in FIG. 6. An area enclosing heating member 422, which also includes areas surrounding density sensor 426 and temperature sensor 424, respectively, is formed into a sensing region.

If the temperature measured in temperature sensor 424 is higher than a predetermined upper limit temperature, an isothermal controller (not shown) stops operation of heating member 422. If the measured temperature is lower than a predetermined lower limit temperature, the isothermal controller (not shown) operates heating member 422. Therefore, the temperature of the solution in the sensing region, which surrounding the heating member, is kept in constant. The sensing region means a region filled with the solution, which is around a position that the density sensor is positioned, and it can be defined as a region within a predetermined distance from the other surface of base frame 410, a region within a predetermined distance from density sensor 426, temperature sensor 424, and heating member 422, or a region surrounded by guide unit 412.

In order to operate the isothermal controller, heating member 422, temperature sensor 424, and density sensor 426, a power source is needed. In this case, an external power source can be connected through power supply line 432 to base frame 410 rather than to use a built-in battery. Also, data output line 434 can be connected to base frame 410 to transfer the density value or any data to an external device through a wire. Power supply line 432 and data output line 434 can be coated with a material that is not affected by the solution to be measured, and can be drawn out into a position that does not disturb the sensing operation and does not interfere with the elements formed in base frame 410. Temperature sensor 424 can be a thermistor or a bimetal, which is relatively small in size compared to other temperature sensors contemporarily available, and is useful in measuring temperature of liquid.

Regarding density sensor 426, an ultrasonic emitting-sensing sensor shown in FIG. 1 or resistance measurement type density sensor shown in FIG. 2 can be used in density sensing device 400 of the present embodiment. It is, however, preferable to use the cantilever type density sensor constructed in the first or the second embodiments of the present invention in order to improve the accuracy of the measurement.

Figure 7:
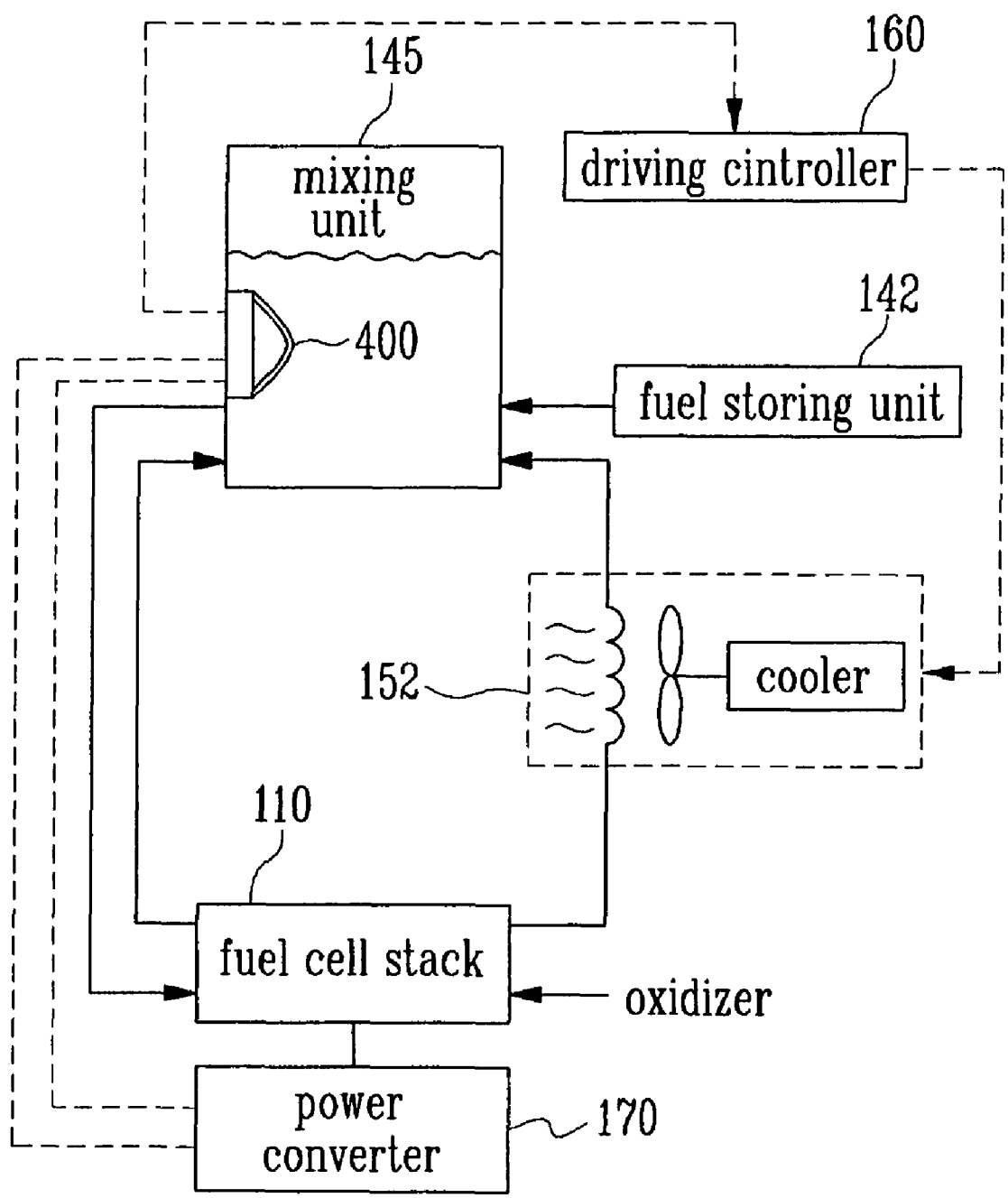
FIG. 7 is a schematic structure diagram showing a fuel cell system that includes a density sensing device of the present invention shown in FIG. 6.

FIG. 7 shows a direct methanol fuel cell system that includes a density sensing device of the present invention shown in FIG. 6. A fuel cell system shown in FIG. 7 has a structure the same as the fuel cell system in FIG. 4. In order to illustrate the position of density sensing device 400 of FIG. 6, only a portion, which includes mixing unit 145, fuel cell stack 110, power converter 170, fuel storing unit 142, heat exchanger 152, and driving controller 160, is illustrated in FIG. 7. Therefore, detailed descriptions of the elements are omitted.

The structure of the present embodiment is not limited to the system that uses methanol for fuel, and can be applied to any fuel cell system that uses an aqueous solution for fuel, such as a fuel cell using ethanol or acetic acid.

Referring to FIG. 7, a direct methanol type fuel cell includes fuel cell stack 110 for generating electricity by electro-chemical reaction between hydrogen gas and oxygen gas, fuel storing unit 142 storing a high density fuel to be supplied to fuel cell stack 110, oxidizer supplier (not shown) for supplying an oxidizer to fuel cell stack 110, heat exchanger 152 for recovering non-reacted fuel exhausted from fuel cell stack 110, and mixing unit 145 for supplying hydrogen-containing fuel, which is generated by mixing the non-reacted fuel exhausted from heat exchanger 152 with the high density fuel exhausted from fuel storing unit 120, to fuel cell stack 110. Herein, heat exchanger 160 and mixing unit 145 form an effluent processor processing the effluent of the stack, and fuel storing unit 142 and mixing unit 145 form a fuel supplier.

The electric energy generated from chemical reaction between hydrogen gas and oxygen in the unit cell of fuel cell stack 110 is converted to have standard voltage and current by power converter 170. The electricity with the standard voltage and current is outputted for application. The output of power converter 170 can charge a secondary cell separately equipped, or can supply power to driving controller 160 or density sensing device 400.

The density sensing device of the present invention can be installed inside mixing unit 145 as shown in FIG. 7, or can be installed inside another units of the system such as pumps. The density sensing device of the present invention also can be installed in the liquid flow path, such as a pipe connecting the cathode of fuel cell stack 110 to heat exchanger 152, a pipe connecting heat exchanger 152 to mixing unit 145, a pipe connecting the anode of fuel cell stack 110 to mixing unit 145, a pipe connecting fuel storing unit 142 to mixing unit 145.

In the case that density sensing device 400 of the present invention 400 is installed in mixing unit 145, the temperature of a sensing region can be kept in constant, even though temperature of mixing unit 145 can vary depending on an operation condition and ambient temperature. For example, the temperature of mixing unit 145 can vary between 65° C. to 75° C. in a direct methanol fuel cell (DMFC). Without density sensing device 400 of the present invention, the temperature of the sensing region also varies according to the temperature of mixing unit 145, which results in inaccurate density measurement. If density sensing device 400 is installed in mixing unit 145, the temperature of the sensing region can be maintained in constant. For example, heating member 422 can be controlled to maintain the temperature of the sensing region at 80° C. Because the temperature (80° C.) of the sensing region is higher than the temperature fluctuation range (65° C. to 75° C.) of mixing unit 145, the temperature of the sensing region is not affected by the temperature fluctuation of mixing unit 145. Therefore, it is possible to maintain a constant temperature at the sensing region, and the measurement of the density is more accurate.

The present invention has an advantage of providing a density sensor at a low cost, and an advantage of accurate measurement of density regardless of ambient temperature. The present invention provides a fuel cell system with a cantilever density sensor having an advantage of accurate measurement of density and low manufacturing cost.

Because the cantilever density sensor can be made in small size, the density sensor of the present invention has an advantage of providing high operation efficiency. The density sensing device of the present invention has an advantage of fast measurement speed. Therefore, the density of fuel is promptly updated, which improves the operation efficiency of the fuel cell system.

Although a few embodiments of the present invention have been shown and described, it would be appreciated by those skilled in the art that changes might be made in this embodiment without departing from the principles and spirit of the invention, the scope of which is defined in the claims and their equivalents.

What is claimed is:

1. A fuel cell system comprises:
a fuel cell stack for generating electric energy through electro-chemical reaction of hydrogen and an oxidizer;
a fuel supplier for supplying a fuel solution containing hydrogen to the fuel cell stack;
an oxidizer supplier for supplying an oxidizer to the fuel cell stack;
a density sensor for measuring density of the fuel solution, the density sensor comprising:
a collision sensor dipped in the fuel solution, the collision sensor detecting collisions of molecules of the fuel solution; and
a variable resistor coupled to the collision sensor, resistance of the variable resistor varying depending on an amount of the collision detected by the collision sensor; and
a driving controller coupled to the density sensor, the driving controller controlling the fuel cell system to maintain a constant density of the fuel solution.

2. The system according to claim 1, further comprising a sensor driver coupled to the collision sensor, the sensor driver driving the collision sensor to vibrate.

3. The system according to claim 1, wherein the collision sensor and the variable resistor are integrally formed.

4. The system according to claim 2, comprised of the collision sensor including a sensing plate, and comprised of the sensor driver comprising:
a piezoelectric member attached on the sensing plate; and
an electrode unit coupled to the piezoelectric member to drive the piezoelectric member.

5. The system according to claim 4, comprised of the electrode unit including a pair of electrodes, one electrode of the pair of electrodes formed on one surface of the piezoelectric member and another electrode of the pair of electrodes formed on another surface of the piezoelectric member.

6. The system according to claim 4, further comprising a pulse supplier for supplying a driving pulse to the electrode unit.

7. The system according to claim 6, wherein the pulse supplier generates the driving pulse by receiving a reference clock of the driving controller.

8. The system according to claim 1, comprised of the density sensor including a density computing unit coupled to the variable resistor, the density computing unit computing value of density from the value of the resistance of the variable resistor.

9. The system according to claim 8, comprised of the density computing unit comprising:
a resistance measurement unit for measuring the resistance of the variable resistor; and
a density converter coupled to the resistance measurement unit, the density converter converting the resistance of the variable resistor into the value of density.

10. The system according to claim 9, comprised of the density converter including a conversion table that includes a relationship between resistance and density, the density converter converting the resistance of the variable resistor into the value of density by looking up the relationship of the conversion table.

11. The system according to claim 8, comprised of the density computing unit comprising:
a resistance measurement unit for measuring the resistance of the variable resistor;
a temperature measurement unit for measuring temperature at a position at which the density sensor is located; and
a density converter coupled to the resistance measurement unit, the density converter converting the resistance of the variable resistor into the value of density.

12. The system according to claim 11, comprised of the density converter including a conversion table that includes a relationship between resistance and density, the density converter converting the resistance of the variable resistor into the value of density by looking up the relationship of the conversion table.

13. The system according to claim 1, further comprising an effluent processor coupled to the fuel cell stack, the effluent processor removing or recycling an effluent of the fuel cell stack.

14. The system according to claim 1, the density sensor further comprising a protective chamber enclosing the collision sensor, the protective chamber protecting the collision sensor from collision with an impurity particle.

15. The system according to claim 1, the density sensor further comprising:

a base frame;

a temperature sensor formed on the base frame, the temperature sensor measuring temperature of a fuel solution of the fuel cell system;

a heating member formed on the base frame, the heating member partly or completely surrounding both of the temperature sensor and the collusion sensor, an area enclosing the heating member being formed into a sensing region, the heating member heating the fuel solution in the sensing region; and an isothermal controller coupled to the heating member, the isothermal controller controlling the heating member in order to keep the output value of the temperature sensor constant.

* * * * *